US00PP25898P2

(12) United States Plant Patent
van Zoest

(10) Patent No.: US PP25,898 P2
(45) Date of Patent: Sep. 15, 2015

(54) *CLEMATIS* PLANT NAMED 'ZO06137'

(50) Latin Name: ***Clematis* hybrid**
Varietal Denomination: Zo06137

(71) Applicant: Jan van Zoest, Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 95 days.

(21) Appl. No.: 13/999,198

(22) Filed: Jan. 28, 2014

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Penny J. Aguirre

(57) ABSTRACT

A new cultivar of hybrid *Clematis*, 'Zo06137' that is characterized by its almost upright facing flowers, its abundance of flowers, its purple flowers that retain their color with very little fading, its sterility, and its cold hardiness to at least U.S.D.A. Zone 5.

3 Drawing Sheets

Botanical classification: *Clematis* hybrid.
Variety denomination: 'Zo06137'.

BACKGROUND OF THE INVENTION

The present invention relates to a new and distinct cultivar of *Clematis* of hybrid origin (Diversifolia Group) and will be referred to hereafter by its cultivar name 'Zo06137'. 'Zo06137' is an herbaceous perennial grown for use as a landscape plant, a flowering potted plant for the terrace, and as cut flower.

'Zo06137' derived from an ongoing breeding program by the Inventor at his nursery in Boskoop, The Netherlands. The goal of the selection was to select a hardy semi-climber with uniquely colored flowers, that was easy to grow and propagate, and that could be grown for different purposes. 'Zo06137' was selected as a single unique plant in 2006 and arose from a controlled cross made in 2003 between unnamed plants from the Inventor's breeding program; the female parent designated as No. 19960251 and the male parent designated as No. 20030161.

Asexual propagation of the new cultivar was first accomplished by internodial stem cuttings under the direction of the Inventor in Boskoop, The Netherlands in 2006. Asexual propagation has determined that the characteristics of the new cultivar are stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zo06137' from other varieties of *Clematis* known to the Inventor.

1. 'Zo06137' exhibits almost upright facing flowers.
2. 'Zo06137' exhibits an abundance of flowers.
3. 'Zo06137' exhibits dark purple flowers that retain their color with very little fading.

4. 'Zo06137' is sterile; no seed is produced.
5. 'Zo06137' is cold hardy to at least U.S.D.A. Zone 5.

'Zo06137' differs from its female parent in having more or less upright flowers while the female parent has nodding flowers. 'Zo06137' differs from its male parent in having flowers that are smaller in size and single with a different flower shape.

'Zo06137' can be most closely compared to the cultivars 'Zobluepi' (not patented) and 'Durandii' (not patented); differences are described in TABLE 1.

TABLE 1

| | Characteristic | Description | 'Zo06137' |
|---|---|---|---|
| 'Zobluepi' | Tepal form | Twisted | Not twisted |
| 'Zobluepi' | Tepal number | 4 | 4-5-6 |
| 'Zobluepi' | Flower shape | Campanulate | Almost spreading |
| 'Durandii' | Flower size | 7-14 cm in diameter | 5-8 cm in diameter |
| 'Durandii' | Flower shape | Fully spreading | Almost spreading |
| 'Durandii' | Leaf | Always simple | Simple or ternate |
| 'Durandii' | Tepals | Strongly ribbed | Not strongly ribbed |

BRIEF DESCRIPTION OF THE DRAWING

The accompanying colored photographs illustrate the overall appearance and distinct characteristics of the new *Clematis*. The photographs were taken of a three year-old plant of 'Zo06137' as grown in a one-gallon container in Boskoop, The Netherlands.

The photograph in FIG. 1 shows a single stem.

Figure 1:
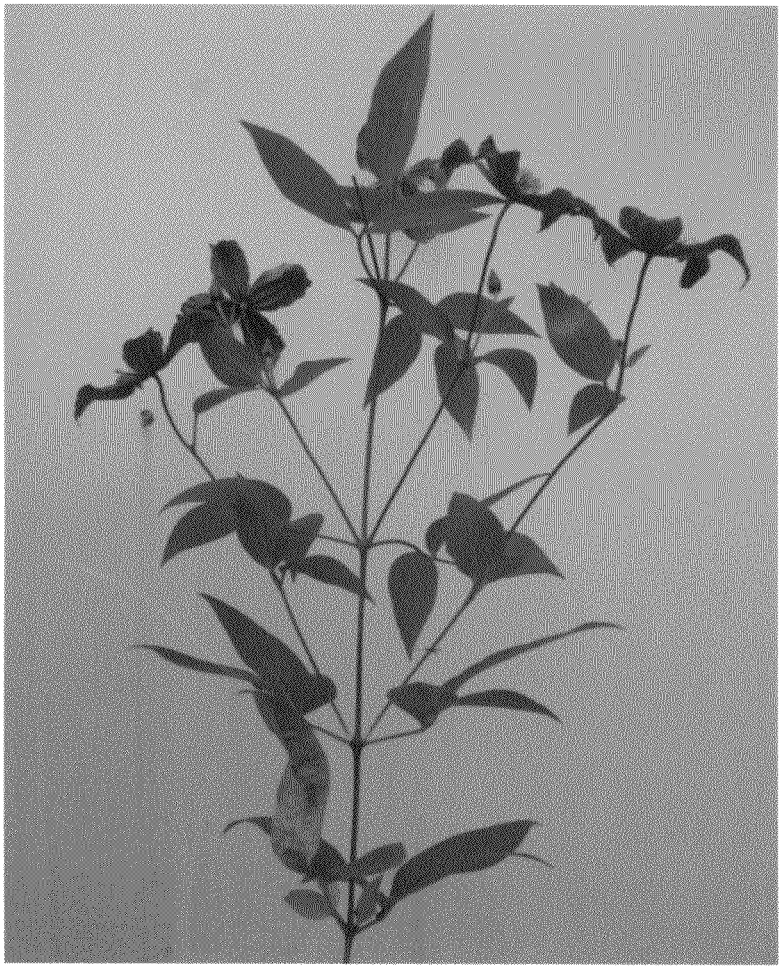
Figure 2:
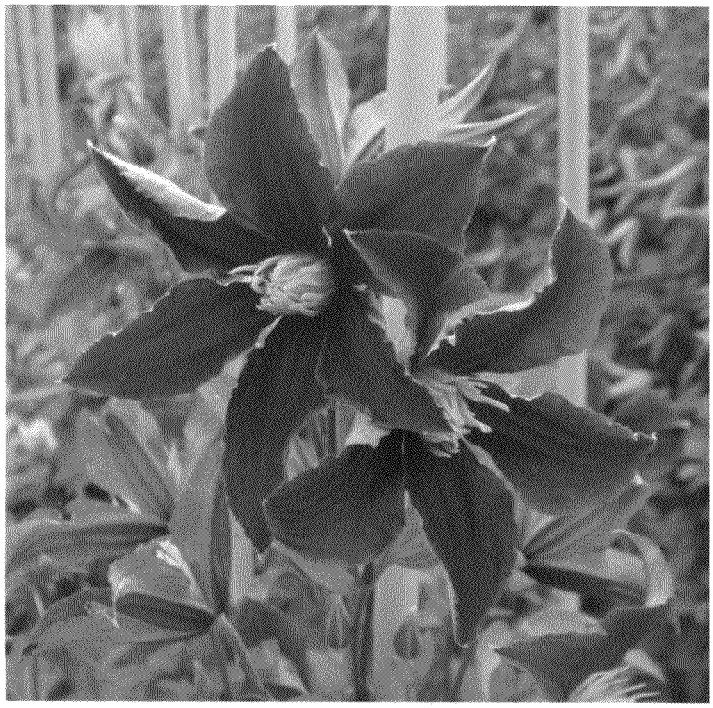

The photograph in FIG. 2 shows the flowering habitus.

Figure 3:
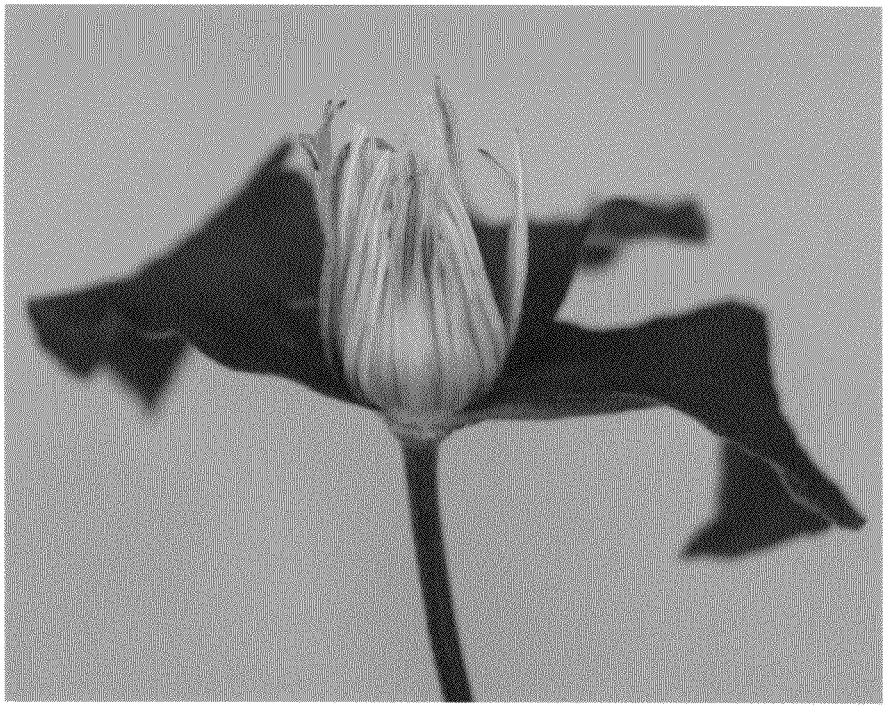

The photograph in FIG. 3 shows the inside of the flower with a close up of the stamens and pistils.

Figure 4:
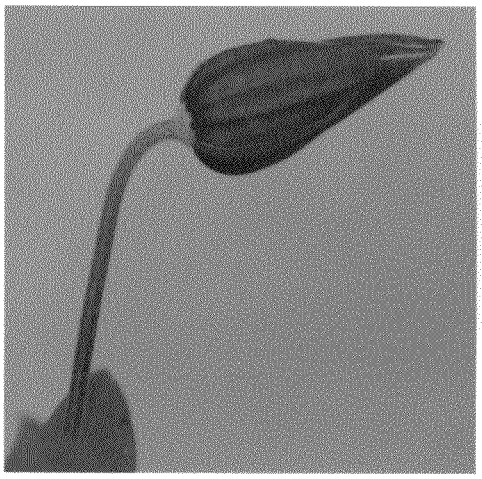

The photograph in FIG. 4 shows the flower bud.

Figure 5:
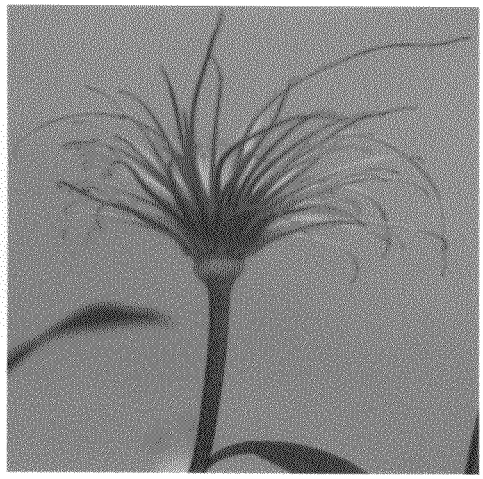
Figure 6:
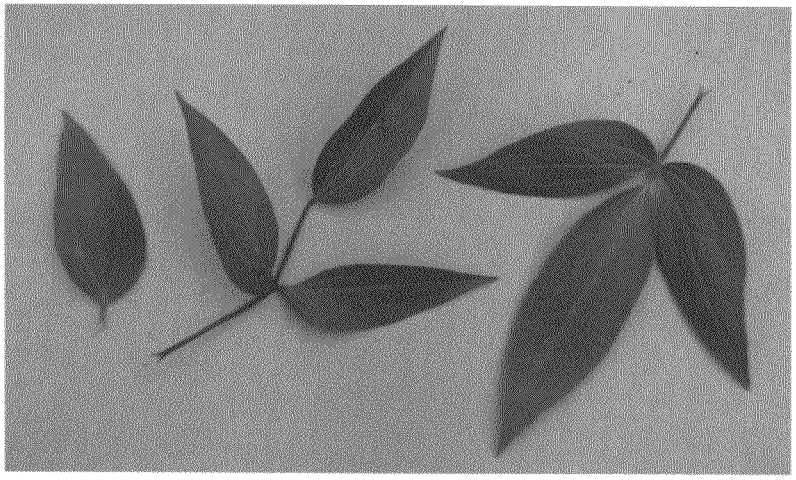

The photograph in FIG. 5 shows the sterile seedhead and the photograph in FIG. 6 shows the upper surface of 3 leaves.

The colors of the photographs are as close as possible with the digital photography techniques available and the color values cited in the detailed botanical description accurately describe the colors of the new *Clematis*.

DETAILED BOTANICAL DESCRIPTION

The following is a detailed description of three year-old plants of *Clematis* 'Zo06137' as grown outdoors in full sun in one-gallon containers at a nursery in Boskoop, The Netherlands. The phenotype of the new cultivar may vary with variations in environmental, climatic and cultural conditions, as the cultivar has not been tested under all possible environmental conditions. The color determination is in accordance with The 2001 R.H.S. Colour Chart, London, England, except where general color terms of ordinary dictionary significance are used.

General description:

*Botanical classification.*—*Clematis* 'Zo06137' (classified in the Diversifolia Group).

*Blooming period.*—From late spring to late summer in The Netherlands.

*Plant type.*—Herbaceous perennial.

*Plant habit.*—Sub-climber.

*Height and spread.*—Three year-old plant is about 20 cm in width at the base and 1 to 1.5 m in height when pruned hard in late winter.

*Cold hardiness.*—At least to U.S.D.A. Zone 5.

*Culture.*—Moist but well-drained soils in full sun with the roots shaded.

*Diseases.*—No susceptibility or resistance to powdery mildew has been observed.

*Root description.*—Fleshy.

Growth and propagation:

*Propagation.*—Internodial soft wood cuttings from vegetative shoots.

*Root initiation.*—Roots develop in 5 weeks in summer under greenhouse conditions.

*Time required for root development.*—75 to 90 days to develop a 7-cm container from a 5-cm cutting.

*Growth rate.*—Vigorous and very free flowering but tidy once planted in the landscape.

Stem description:

*Shape.*—Round and strongly 6-ribbed.

*Stem color.*—172B in color.

*Stem size.*—About 1 to 1.5 m in length (including peduncle and terminal pedicel), an average of 1 to 3 mm in diameter.

*Stem surface.*—Sparsely covered with hairs.

*Internode length.*—Ranges from 3 to 10 cm.

*Branching.*—Branching from the base.

Foliage description:

*Leaf arrangement.*—Opposite.

*Leaf division.*—Simple or ternate (simple leaves are similar to leaflets).

*Leaf size.*—Up to 15 cm in length (including petiole, up to 10 cm in length without petiole) and 10 cm in width when ternate.

*Leaflet size.*—Up to 8 cm in length and 3.5 cm in width.

*Leaf attachment.*—Petiolate.

*Leaflet attachment.*—Sessile to petiolulate.

*Leaflet shape.*—Narrow elliptic to lanceolate.

*Lealet base.*—Cuneate on terminal leaflet or single leaf, oblique at side leaflets.

*Leaflet apex.*—Acuminate.

*Leaflet fragrance.*—Clearly a "sharp" fragrance when crushed.

*Leaflet venation.*—Upper surface slightly reticulate, lower surface less reticulate.

*Leaflet margin.*—Entire.

*Leaflet surface.*—Upper surface; glabrous, lower surface; glabrous with a few sparse hairs on the main veins and margin.

*Leaflet color.*—Upper surface; 146A, lower surface; 147B.

*Petioles.*—1 to 5 cm in length, 1 mm in diameter, 146B and suffused with 59B, round in shape but canaliculate on upper surface, surface sparsely hairy.

*Petiolules.*—Sessile to 3 cm in length, surface mostly glabrous with just a few hairs.

Inflorescence description:

*Inflorescence type.*—Solitary or a 3 to 5 flowered dichasial cyme.

*Inflorescence arrangement.*—Terminal and axillary on young shoots.

*Peduncles.*—Up to 10 cm in length and up to 0.2 cm in width, 146C and suffused with N77, round, surface slightly 6-ribbed, surface short hairs.

*Pedicels.*—Up to 9 cm in length and 0.1 to 0.15 cm in width, 79A, round and slightly ribbed, surface has short hairs that are more dense towards the flower.

*Flower buds.*—More or less upright with a slightly nodding stage, lanceolate in shape, apex acuminate, base obtuse, N92D in color with N92A at the base, surface with a few long hairs and villous seams.

*Flower fragrance.*—Just slightly.

*Lastingness of the flowers.*—Individual flowers last up to about 6 to 10 days until the first tepal drops, followed later by the stamens.

*Flower quantity.*—Up to 15 per stem.

*Flower type.*—Single, open campanulate to almost spreading.

*Flower aspect.*—More or less upright.

*Flower size.*—5 to 8 cm in diameter.

*Flower sex.*—Bisexual.

*Tepal number.*—4, 5 or 6.

*Tepal shape.*—Narrow elliptic to oblanceolate.

*Tepal apex.*—Acuminate.

*Tepal base.*—Cuneate.

*Tepal margin.*—Entire.

*Tepal surface.*—Inner surface; glabrous, outer surface; glabrous with a few hairs in the middle and villous margin.

*Tepal color.*—Inner surface; N89A, flushed with N92A at the margin and fading to N89C, outer surface; 86A in color and fading to N88B with 86B veins.

*Tepal size.*—Up to 5 cm in length and 2.3 cm in width.

Reproductive organs:

*Gynoecium.*—Average of 50 to 70 pistils, up to 1.3 cm in length, ovary 145B in color with short hairs on surface, style is 144D in color with a bit of violet 93D near stigma and silvery plumose, stigma is 155B in color and straight.

*Androcoecium.*—Filaments are 0.4 to 1.2 cm in length, 0.1 to 0.125 cm in width and linear in shape, surface is glabrous with a few hairs below the anthers, the outer are 150D in color with a bit of violet N89B at the base; anthers are 0.5 cm in length, 1 mm in width, linear in shape, and 4D in color, connective is short elongated, apex acute, surface glabrous and 11A in color.

*Seed.*—Seed is not formed, observed to be sterile.

It is claimed:

1. A new and distinct cultivar of *Clematis* plant named 'Zo06137' as herein illustrated and described.

* * * * *